(12) United States Patent
Elias

(10) Patent No.: US 7,822,462 B2
(45) Date of Patent: *Oct. 26, 2010

(54) DIAGNOSIS DEVICE AND METHOD

(76) Inventor: Ilan Elias, Dillenburgerstrasse 29A, 60439 Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/115,972

(22) Filed: Apr. 27, 2005

(65) Prior Publication Data

US 2006/0020196 A1  Jan. 26, 2006

Related U.S. Application Data

(63) Continuation-in-part of application No. 10/375,717, filed on Feb. 27, 2003.

(30) Foreign Application Priority Data

Apr. 27, 2004 (DE) ................. 10 2004 020 783

(51) Int. Cl.
*A61B 5/05* (2006.01)
*A61B 6/00* (2006.01)
*A47B 13/00* (2006.01)

(52) U.S. Cl. ............... 600/415; 600/427; 5/601; 378/20

(58) Field of Classification Search ......... 600/415, 600/427; 5/601; 324/326; 378/20
See application file for complete search history.

(56) References Cited

U.S. PATENT DOCUMENTS 5,072,247 A * 12/1991 Bovee ................. 396/59

| 5,085,219 A | 2/1992 | Orendahl et al. |
| 5,154,178 A | 10/1992 | Shah |
| 5,184,074 A | 2/1993 | Arakawa et al. |
| 5,442,858 A | 8/1995 | Wolters et al. |
| 5,445,152 A | 8/1995 | Bell et al. |
| 5,461,314 A | 10/1995 | Arakawa et al. |
| 5,520,181 A | 5/1996 | Krieder et al. |
| 5,533,082 A * | 7/1996 | Gronemeyer et al. ......... 378/20 |

(Continued)

FOREIGN PATENT DOCUMENTS

DE  295 14 603 U1  2/1997

(Continued)

OTHER PUBLICATIONS

International Preliminary Report on Patentability dated Nov. 1, 2006, 10 pages.

(Continued)

*Primary Examiner*—Eric F Winakur
*Assistant Examiner*—Michael T Rozanski
(74) *Attorney, Agent, or Firm*—Cantor Colburn, LLP

(57) ABSTRACT

A diagnosis device having a device for producing a series of images, such as a computer tomography device or an ultrasound device. There is also a device for the passive movement of an object and a device that can be stereotactically moved independent of the passive movement object, wherein this stereotactial movement object can be driven by a motor. These two devices can be arranged on or in the diagnosis device to perform a treatment or examination. By controlling the diagnosis device, it is possible to produce a series of images in real time during a passive movement of an object or of the device for performing a treatment or examination.

106 Claims, 4 Drawing Sheets

U.S. PATENT DOCUMENTS

| | | | |
|---|---|---|---|
| 5,541,515 A | | 7/1996 | Tsujita |
| 5,541,516 A | | 7/1996 | Rider et al. |
| 5,577,503 A | | 11/1996 | Bonutti |
| 5,724,970 A | | 3/1998 | Votruba et al. |
| 5,742,136 A | * | 4/1998 | Ono et al. ............... 318/135 |
| 5,743,264 A | | 4/1998 | Bonutti et al. |
| 5,754,046 A | | 5/1998 | Busch et al. |
| 5,772,595 A | | 6/1998 | Votruba et al. |
| 5,851,182 A | * | 12/1998 | Sahadevan ............... 600/407 |
| 5,899,859 A | | 5/1999 | Votruba et al. |
| 5,899,860 A | | 5/1999 | Pfeiffer et al. |
| 5,907,664 A | * | 5/1999 | Wang et al. ............... 700/251 |
| 5,931,781 A | | 8/1999 | De Boer |
| 5,967,980 A | | 10/1999 | Ferre et al. |
| 6,138,302 A | | 10/2000 | Sashin et al. |
| 6,249,695 B1 | * | 6/2001 | Damadian ............... 600/427 |
| 6,411,187 B1 | | 6/2002 | Rotem et al. |
| 6,499,160 B2 | * | 12/2002 | Hand et al. ............... 5/608 |
| 6,582,381 B1 | | 6/2003 | Yehezkeli et al. |
| 6,590,391 B1 | | 7/2003 | Shudo et al. |
| 7,221,159 B2 | * | 5/2007 | Griffiths et al. ........... 324/318 |
| 7,502,641 B2 | * | 3/2009 | Breen ...................... 600/415 |
| 2001/0029330 A1 | | 10/2001 | Nose et al. |
| 2001/0039378 A1 | | 11/2001 | Lampman et al. |
| 2002/0164903 A1 | * | 11/2002 | Chuang ..................... 439/620 |
| 2003/0097060 A1 | | 5/2003 | Yanoff et al. |
| 2003/0184296 A1 | * | 10/2003 | Elias ........................ 324/318 |

FOREIGN PATENT DOCUMENTS

| | | |
|---|---|---|
| DE | 197 32 784 C1 | 3/1999 |
| DE | 696 10 176 T2 | 9/2000 |
| DE | 100 30 507 | 1/2002 |
| JP | 1-242056 A | 9/1989 |
| JP | 3-178638 A | 8/1991 |
| JP | 2000/151175 A | 5/2000 |
| WO | WO 00/25692 A1 | 5/2000 |
| WO | WO 00/28882 A2 | 5/2000 |
| WO | WO 01/045564 | 6/2001 |
| WO | WO 03/041057 | 5/2003 |
| WO | WO 03/082107 | 10/2003 |
| WO | WO 2004/004570 | 1/2004 |

OTHER PUBLICATIONS

Butts et al., "Real-Tme MR Imaging of Joint Motion in an Open MRI Imaging Scanner", RSNA, 83rd Scientific Assembly and Annul Meeting, Chicago, IL 1997, p. 387, paper No. 1041.

Dietrich et al., Extending the coverage of true volume scans by continuous movement of the subject, 1999 ISMRM Proc., p. 1653.

Johnson et al., "Total-Body MR Imaging in as Little as 18 Seconds", Radiology 202 (Jan. 1997), No. 1, pp. 262-267.

Tacke et al., "Eine Stufenlose pneumatische Beuregungsvorrichtungs fur die dynamische MRT der Halswirbeisauale", Forstr. Rongenser 171 (1999) pp. 249-253.

Quick et al., "Real-Time MRI of Joint Movement with TrueFISP", J. Mag. Res. Imaging, vol. 15, pp. 710-715 (2002); also presented at the 9th Annual meeting of ISMRM, Glasgow, Scotland, Apr. 21-27, 2001, p. 2131.

Muhle et al., "Kinematic CT and MR Imaging of the patellofemoral joint", Eur. Radiol. 9, pp. 508-518 (1999).

Beaulieu et al., "Glenohumeral Relatonships during Physiologic Shoulder Motion and Stress Testing: Initial Experience with Open MR Imaging and Active Imaging-Plane Registration,". Radiology, 1999, vol. 212, No. 3, pp. 699-705.

Quick et al., "Real-Time MRI of Joint Movement with True FISP", Proc. Intl. Soc. Mag. Reson. Med. 9 (2001), p. 2131.

* cited by examiner

DIAGNOSIS DEVICE AND METHOD

CROSS REFERENCE TO RELATED APPLICATIONS

This application hereby claims priority under 35 U.S.C. 119 from German Patent No. DE 102004020783.6 filed on Apr. 27, 2004. This application is a continuation in part application and claims priority from U.S. patent application Ser. No. 10/375,717 filed on Feb. 27, 2003.

BACKGROUND OF THE INVENTION

Field of the Invention

The present invention relates to a diagnosis device having a device for producing a series of images and a device for producing a passive movement of an object. This device can have a motor driven support surface, which can be pivoted about at least one axis. The surface can be used to hold at least one object, or one part of an object wherein this object can be moved into the device for producing a series of images.

To examine human, animal or plant joints, in a biomechanical manner, a magnetic resonance tomograph (MRT) can be used to provide a representation of this soft structure. Thus, the movement or progression of a healthy joint having sinews, cartilage or similar structure can be studied using this method. For this purpose, body parts need to be positioned in different positions and in particularly defined ways. Thus, studies using magnetic resonance imaging or tomographs frequently occur when testing the material behavior of various objects.

Until now, static snapshots and static images can be produced in different positions wherein these positions are adjusted manually using a mechanism. Then the resulting images are a result of an image loop (cine mode). This method is known from U.S. Pat. No. 5,541,516 and U.S. Pat. No. 5,899,859 incorporated herein by reference. However, this method is extremely time consuming, and can thus only be used in individual cases. Thus, the possibilities of modern magnetic resonance tomograph, in this case can only be used in individual cases wherein the possibilities of modern magnetic resonance tomograph which include very fast image taking are not fully utilized.

Thus this process is not completely effective in examining materials, objects or body parts using a magnetic resonance tomograph, which can include both the osseous and the cartilaginous parts.

In addition, not all of the damage to objects, or illness or injuries of the human body can be detected with a snapshot particularly since it has not been possible to produce images during a body movement that are of sufficient quality. This result has the negative effect both on precise materials research and clinical diagnostics since the probability and sensitivity of determining existing damage or pathological findings of various structures is not optimally possible and may not be possible at all. This is because in contrast to X-ray examinations, there are no rigidly defined reproducible settings for representing real time movements in magnetic resonance tomography until now.

Thus, due to the strong magnetic field in a magnetic resonance tomograph, a conventional movement apparatus is not possible.

In this case, there is a manipulator for positioning medical instruments on a patient in a magnetic resonance tomograph (MRT) or a computer tomograph (CT) wherein the disclosure of which is known from DE 100 30 507A1. Thus, to perform an operation on a patient using this manipulator, the patient must be held or forced to lie quietly on a patient platform, so that no injuries to the patient can occur.

There is also a known device for producing passive movement on a patient that is known from International patent publication WO 03/082107. With this design, there is a magnetic resonance tomograph, wherein the influence and density of these atoms and relaxation times for magnetization of the materials are recorded via a strong magnetic field and then reconstructed via a series of calculations to produce a cross-sectional image using a computer. Thus, different materials can be represented with different but sufficiently good results using magnetic resonance tomography. Because the scanning times of a MRI or a MRT are comparatively long, involuntary movements or natural body movements such as respiratory or swallowing movements can cause image errors called artefacts that reduce the informational value for a diagnosis. In addition, the time duration of the examination can be extended by this requirement for passive movement.

BRIEF DESCRIPTION OF THE INVENTION

An embodiment of the invention relates to a diagnosis device wherein body parts of a patient or objects can be examined within a short or relatively short period of time, wherein treatment can be performed at the same time as well if necessary.

Thus, to achieve this goal, an embodiment of the invention relates to a device for producing a series of images which includes a computer tomography device, an ultrasound device, a gamma camera, a thermography device, an X-ray device, a sonography device or any other image producing device. With this design, at least one device can move an object stereotactically, independent of the imaging device, while being driven by a motor. This device is designed to perform treatment or examination, so that the drive for pivoting the support surface and the drive for the stereotactic device such as a scalpel which is for performing a treatment or examination, is controlled via a control unit or, so that a series of images is produced in real time during a passive movement of an object or of a device for performing a treatment or examination.

With this design, the images are clearly produced more quickly than with a conventional production model, wherein there is a sequence of individual images between which the object is moved between these images. Thus, a series of images can be obtained via film which shows the examined object not at rest, but during a passive movement of the object or of the device for performing a treatment or examination. The passive movement occurs because while this for example, patient is at rest, another device is used to move a patient's body or body party in a particular manner.

With this design, these images are produced more quickly than with a conventional production of a sequence of images wherein between the production of these images, an object is moved in each instance.

Thus, as a result, a series of images can be obtained such as with a motion picture of film, which shows an examined object that is not at rest but imaged during movement. Thus, diagnosis or movement or human, plant or animal parts can be examined during the filming of this material.

Some biomechanical processes can only be explained when examining these actual movement sequences, for example in a joint, which was not previously known as possible in the cine mode until now, wherein this mode includes stringing together a series of images. In material property research, the initiation of a crack or the propagation of a crack is a dynamic process wherein this can be frequently assessed only by means of real time images but not using static images.

This device can preferably be a spiral (or helical) scanning computer tomograph, or an electron beam computer tomograph. With a spiral (or helical scanning) computer tomograph the scanning of a patient or of an object can take place continuously via a circling x-ray tube, while a support surface such as a patient platform is moved.

Thus, while this examination time is significantly reduced, the radiation dose can also be reduced. At the same time, the diagnostic information is increased because image defects caused by respiration or other involuntary movements no longer occur. This phenomenon is true for examinations of a chest cavity, the lungs or an abdominal space. This feature applies in the same manner for diagnosis in the region of the neck and the head that can be quite significant for orthopedic questions. Thus, a modern sixteen cell spiral (or helical scanning) computer tomograph can produce a plurality of images in a very short period of time, which then allows for the representation of an organ from different spatial perspectives. In this case, 16 data lines are recorded during one revolution of an X-ray tube that therefore lasts approximately 0.4 seconds. Such a spiral tomograph can then be suited for taking real time images of a defined passive movement for the diagnosis of joint mechanics, osseous or cartilaginous sliding movements, fracture gap manipulations, or other movement analyses.

In this case, electron beam tomographs can also be well suited for examinations, wherein these tomographs have very rapid image taking times of 100 ms. Thus, using these types of devices, it is thus possible to slice images of moving organs in real time. Alternatively, a device for producing a series of images can also be configured as a positron emission tomograph (PET), a single photon emission computer tomograph (SPECT), a gamma camera for static or dynamic scintigraphy, a digital infrared thermography device, a dynamic surface thermography device, or a digital X-ray device.

Image artefacts can be further prevented wherein the drive for pivoting the support surface or the treatment of the examination device can have a piezoelectric motor. In addition to using the piezoelectric motor, it is also possible to use a pneumatic or hydraulic drive as well.

The drive for pivoting the support surface is preferably controlled by a control unit, which is grounded and shielded against magnetic radiation. The drives can be connected with a control unit by way of lines that are grounded and shielded against magnetic radiation or via a wireless remote control such as an infrared remote control. Using this diagnosis device, these movements can then be set electronically, with automatic control in the same reproducible positions at all times. Thus, the position between the body part, the body part to be examined, and the diagnosis device can remain the same during the entire diagnostic procedure. At the same time, precisely defined movements can be made during the image taking process wherein these movements are controlled by motors for the first time. This feature then allows the operator of the imaging apparatus to produce a specific image in a targeted manner and to also represent the movement itself in a real time image.

Control of this support surface can be further improved wherein this control unit can have at least one sensor, such as an optical encoder to detect the position of a support surface or a motor.

In another embodiment of the invention, a support surface can be pivoted about two axes, independent of each other with a motor drive. In this way, the physiological movements or sequences of different body parts to be examined can be represented in an even better manner.

The physiological movement of an ankle joint can be imaged particularly well using a device wherein the support surface can be pivoted about a first horizontal axis and about a second axis that is inclined by about 35 degrees in a horizontal plane relative to a vertical plane, and by about 18 degrees in the saggital plane. This inclination of the second axis corresponds to the average geometric axis of a lower ankle joint determined by Van den Bogard.

Thus with this design, the pressure forces acting on an ankle can be therefore reproduced during an examination in a diagnosis device wherein there is a means for fixing of a body part of the patient in place on a support surface, wherein this support surface can be moved relative to a means for fixation in at least some regions.

This support surface can be preferably moved pneumatically or hydraulically relative to a means for fixing the body part in place. Thus, a step by step compression of a body part to be examined can take place which results in a change in a configuration of individual parts of a body, which then allows for the reproduction of stresses while running.

BRIEF DESCRIPTION OF THE DRAWINGS

Other features of an embodiment of the present invention will become apparent from the following detailed description considered in connection with the accompanying drawings. It should be understood, however, that the drawings are for the purpose of illustration only and not as a definition of the scope and extant of the invention.

In the drawings, wherein similar reference characters denote similar elements throughout the several views.

DETAILED DESCRIPTION OF DISCLOSED EMBODIMENTS

Figure 1:
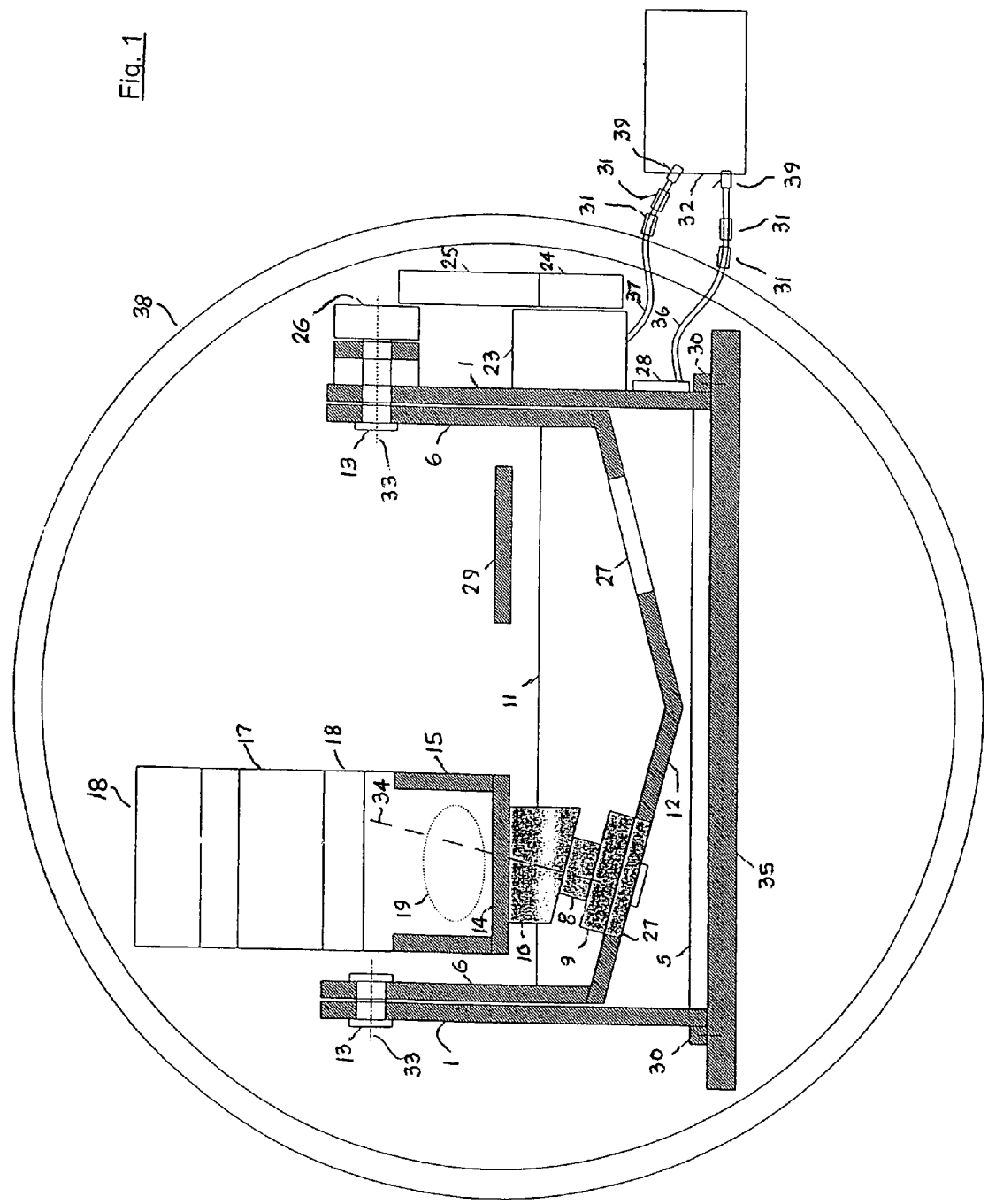
FIG. 1 is a longitudinal section through an imaging passage of a diagnosis device.
Figure 2:
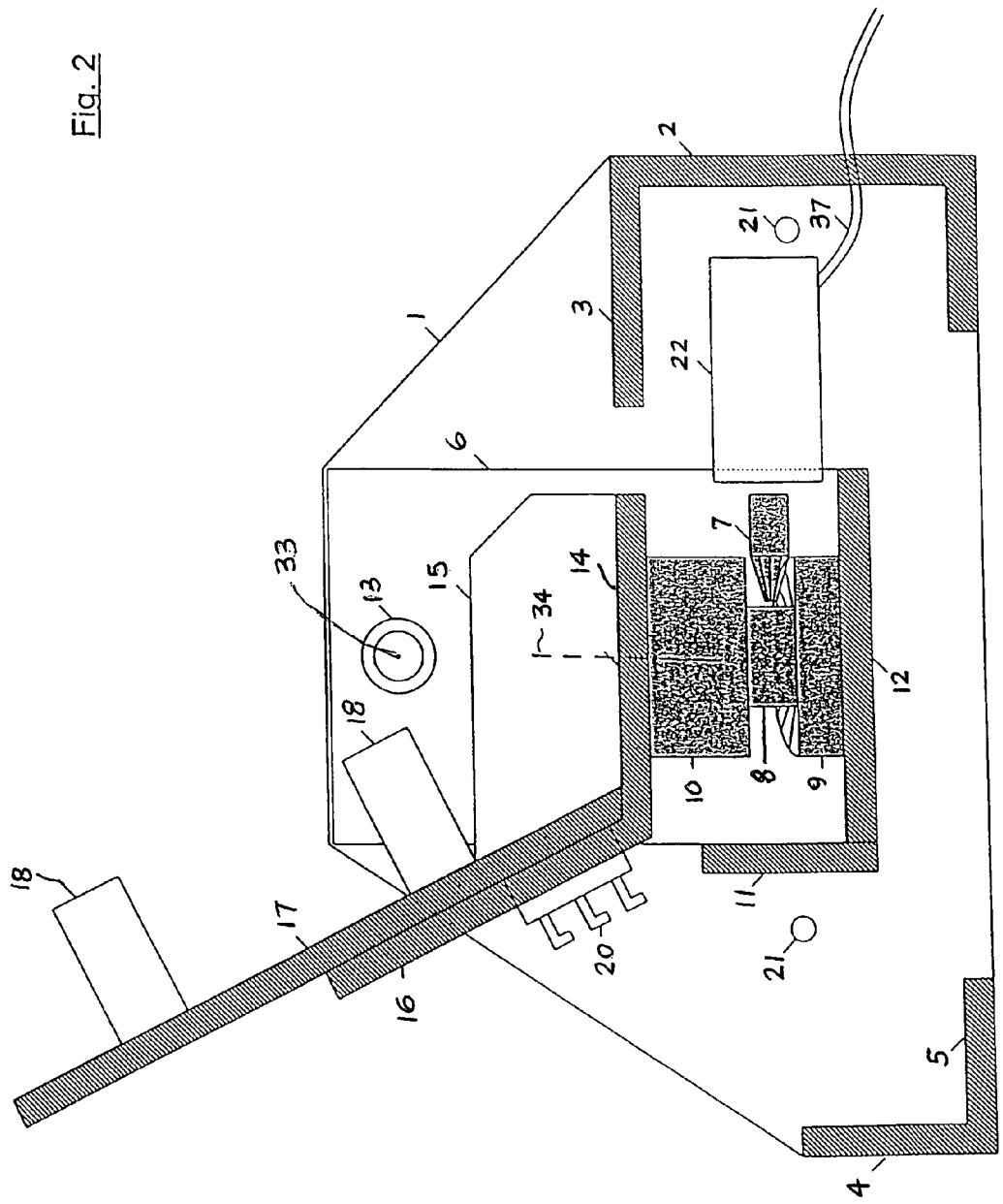
FIG. 2 is a side view of the device disposed perpendicular to a section plane of FIG. 1.
Figure 3:
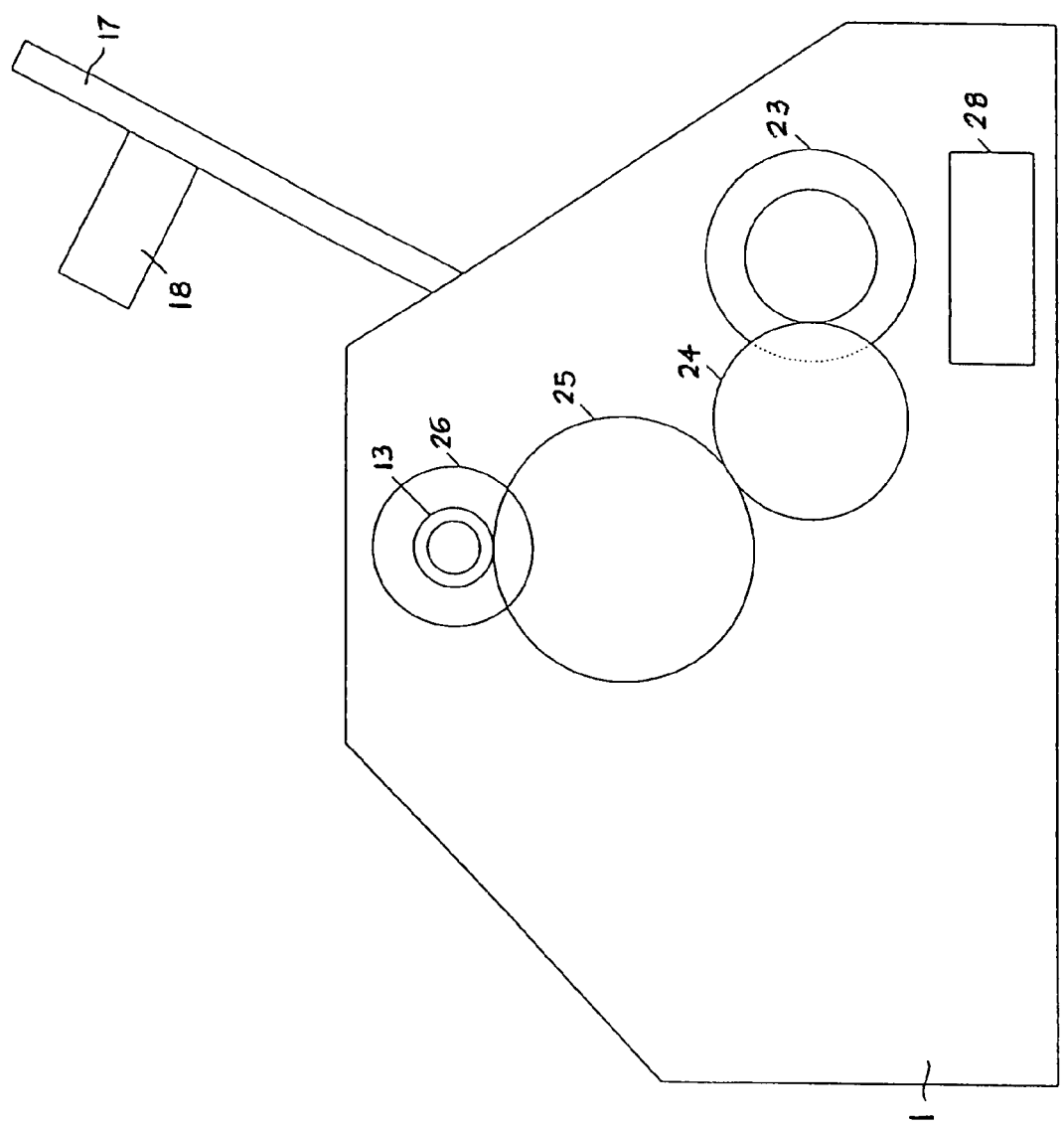
FIG. 3 is a side view of the device shown in FIG. 2.

Referring to the drawings, FIG. 1 shows a diagnosis device which is positioned to produce a passive movement to examine an ankle joint. However, in this setting, it is also possible to examine other body parts as well, or other objects made from any desired materials using this device. With this design, this device has a support surface 14, for a heel of a foot and a support surface 17 for a sole of a foot which runs at an angle to heel support surface 14. The inside and outside ankle bone of the foot are stabilized via side walls 15, while the support surface 17 for the sole of the foot is held on a rear wall 16. FIG. 1 shows that the foot to be examined is indicated by reference numeral 19.

In this case, the device for producing passive movement can be attached to a patient platform 35 via a connecting unit 30 as shown in FIG. 1. Thus, with this design, a patient can lie on his or her back and then be pushed into an imaging passage 38 of an imaging device using a patient platform wherein this device is arranged at one end of this patient platform 35. With this design, the foot can be held in place using buckles 18. However, the foot that is not being examined can be placed on another support surface 29 so that it is not included in the examination.

This device for producing a passive movement can be positioned on patient platform 35 and can include two vertical side walls 1, and a vertical front wall 2. This vertical front wall can make a transition into a horizontal front wall 3. On the side opposite vertical front wall 2, there is a vertical rear wall 4, which is connected with a horizontal rear wall 5.

There is also another vertical wall 6 that is joined to side walls 1, in an articulated manner so that it can pivot around a horizontal axis 33 via ball bearings 13, wherein this wall runs parallel to side walls 1. With this design, the vertical walls 6 are connected to a rear wall 11 and a V-shaped bottom wall 12.

There are two recesses 27 which are formed in a V-shaped bottom wall 12, wherein an attachment unit 9 can be positioned. This attachment unit 9 has an intermediate part 8 that carries another attachment unit 10 having a gear wheel, wherein on this support surface for the heel as well as with the rear wall 16 has a support surface 17 for the sole of the foot which can be rotated relative to an attachment unit 9 via another attachment unit 10. In this case there is an attachment support surface 14, for a heel, wherein a rear heel 16 on the support surface 17 for the sole of the foot can be rotated about an axis 34 which is inclined at about a 35 degree angle from a horizontal plane. This device is also angled at about 18 degrees in the sagittal plane, relative to a vertical alignment. This is via a V-shaped incline bottom wall 12 and a corresponding configuration of attachment units 9 and 10.

These attachment units 9 and 10 have a piezoelectric motor 22, wherein this motor has a gear wheel 7 having a conical tip which can move this attachment unit 10 relative to attachment unit 9. This piezoelectric motor 23 has a vertical side wall which has a first gear wheel 26, and which is connected to side walls 6 so as to rotate with it via another gear wheel 25. In this way, side walls 6 can pivot relative to side walls 1 when driven by motor 23.

There is also a pressure valve unit 20 that has a support surface 17 for a sole of a foot that can be displaced relative to a rear wall 16, wherein this device can be arranged on this rear wall 16. In this way, a pressure on the sole of the foot can be produced in an infinitely adjustable manner.

There are two optical encoders 21, which can detect the position of the side walls 6 relative to side walls 1, wherein these encoders 21 can be passed on to an electrical box 28, via lines which are not shown. This box is connected with control unit 32 via a shielded cable 36. These motors 22 and 23 are controlled by a control unit 32 via shielded cables 37. Outside the imaging passage 38, of this imaging device, ferrite cores 31 are arranged on shielded lines 36 and 37. The connection of lines 36 and 37 with control unit 32 occurs via cable plugs 39 that are also shielded.

The materials that can be used for producing a passive movement produce no image artefacts that would make a diagnosis impossible. This is for example, VA4 stainless steel screws and threads, aluminum plates pins, screws and air pressure eyes made of brass, plastic screws and glass and ceramic ball bearings. With this design, the use of polyoxymethylene semi tools (POM) are particularly advantageous because plastic can absorb a high frequency field HF so that this material does not produce an interference radiation.

With the embodiment of the device for producing passive movement, these images can be produced so that a passive movement is also produced. Thus, it is possible to produce both cinematic real time images during the passive movement of a body part, wherein static images from different positions within imaging passage 38, of an imaging device are shown for research and routine clinical diagnostics. These real time images of the movement sequence significantly expand the possibilities of use of this imaging device.

Figure 4:
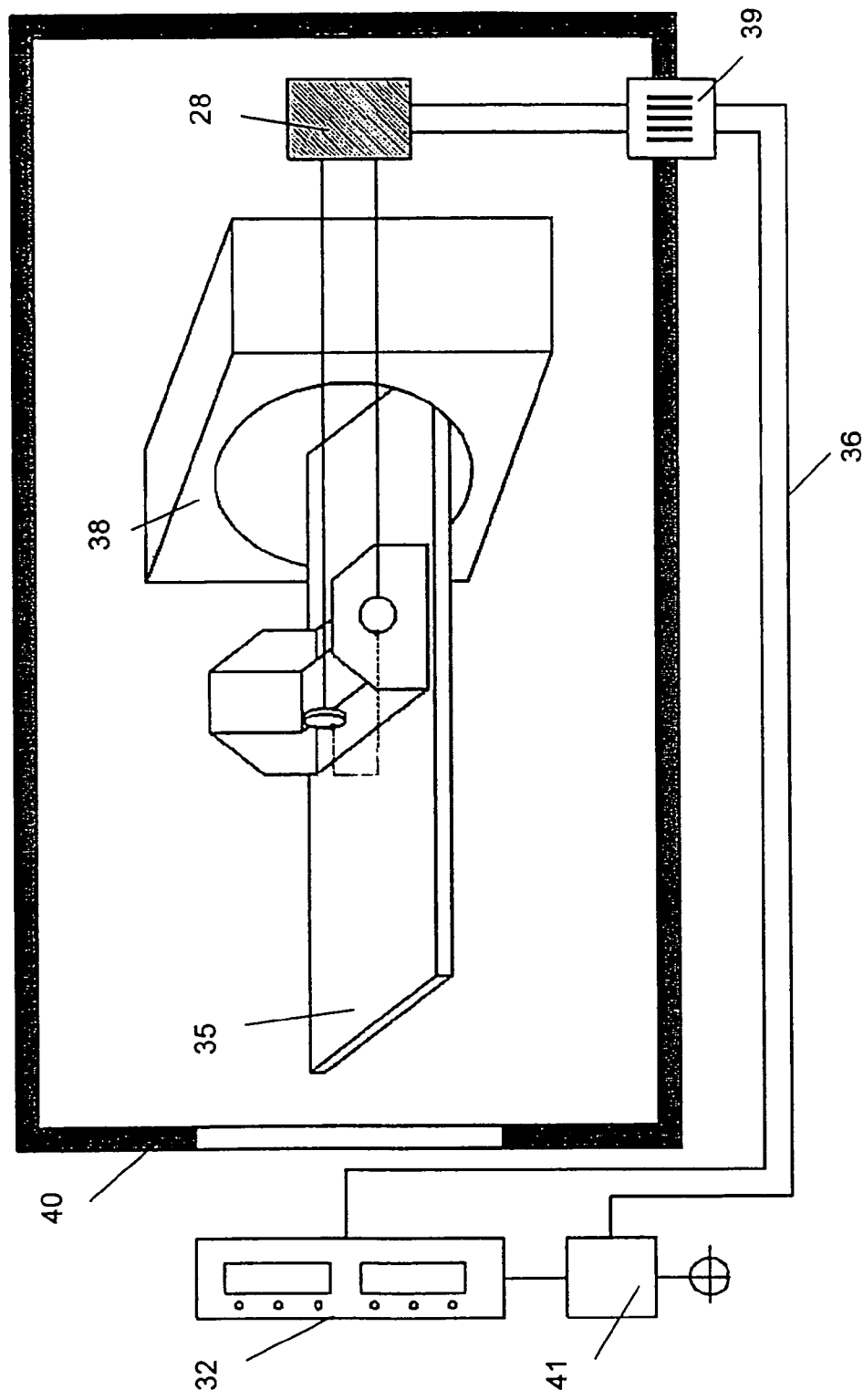
FIG. 4 is a perspective view of a diagnosis device shown as another embodiment.

FIG. 4 shows imaging passage or enclosure 38 that houses a patient platform 35. Patient platform 35 can be moved and it is arranged in a computer tomograph room 40, wherein there is a control unit 32 and power part 41 with a connection to a power source disposed outside of the room. In FIG. 4 the device for producing passive movement is provided with energy or power via cables 36 and 37. However, it is also possible to provide energy without these cables.

Accordingly, while a few embodiments of the present invention have been shown and described, it is to be understood that many changes and modifications may be made thereunto without departing from the spirit and scope of the invention as defined in the appended claims.

What is claimed is:

1. A method for acquiring a continuous real-time image of an object comprising:
   providing means for acquisition of the image of the object;
   providing a non-ferromagnetic device for supporting the object to be imaged;
   providing a non-ferromagnetic means for applying a defined reproducible passive movement to pivot the object independently about a first and second axis to apply pressure and/or pivoting and/or movement to the object or one body part of the object;
   providing a unit for controlling the device;
   disposing the unit exterior to the means for acquisition of the image;
   providing between the unit and the means for imaging and exterior to the means for imaging an electrically grounded connection;
   providing between the unit and the means for imaging and exterior to the means for imaging a connection shielded against magnetic flux; and
   acquiring the image continuously in real-time during imaging while or during pivoting and/or applying pressure and/or movement to the object or one body part of the object.

2. The method of claim 1 wherein the application of pressure and/or pivoting and/or movement of the object is about two axes, the axes being at an incline with respect to each other.

3. The method of claim 2 comprising sensing the pivoting of the object or the one body part of the object on at least one axis.

4. The method of claim 1 comprising sensing the applied pressure and/or pivoting and/or movement.

5. The method of claim 1 wherein the first axis is inclined at about 35 degrees to the second axis.

6. The method of claim 1 wherein the first axis is inclined at an angle of about 35 degrees to a horizontal plane and inclined at an angle of about 18 degrees in a longitudinal plane relative to a vertical axis.

7. The method of claim 1 comprising disposing the object or the one body part of the object in a passage selected from a the group consisting of a magnetic field, nuclear Of and emitted radiation.

8. The method of claim 1 comprising acquiring the image in a magnetic resonance modality.

9. The method of claim 1 comprising acquiring the image in a computer tomography modality.

10. The method of claim 1 comprising acquiring the image in an X-ray modality.

11. The method of claim 1 comprising acquiring the image in an ultrasound modality.

12. The method of claim 1 wherein the providing of the passive movement applied pressure and/or pivoting and/or movement imitates a physiological movement of the object or the one body part of the object.

13. The method of claim 1 wherein the providing of the passive movement applied pressure and/or pivoting and/or movement is adjustable.

14. The method of claim 1 comprising choosing material for the device that will avoid interferences or artifacts in the imaging.

15. The method of claim 1 wherein the applied pressure and/or pivoting and/or movement is selected from the group consisting of continuous, constant, adjustable, step-by-step, variable and a combination thereof.

16. The method of claim 1 wherein the passive movement is pressure applied and/or pivoting and/or movement to the object or the body part of the object while the object or the body part is at rest.

17. The method of claim 1 wherein the object or the one body part of the object is an anatomical body part having a joint.

18. The method of claim 1 wherein the object is a non-human body or one body part of the non-human object.

19. The method of claim 1 wherein the pivoting and/or the applied pressure and/or movement reproduces stress on another part of the object.

20. The method of claim 1 wherein the means for acquisition has a closed bore imaging passage.

21. The method of claim 1 wherein the pivoting and/or the applied pressure and/or movement reproduces stress on a body of the object or the one part of the body.

22. The method of claim 1 wherein the non-ferromagnetic means is hydraulic or pneumatic.

23. The method of claim 1 wherein the non-ferromagnetic means is a piezo-electromotor.

24. The method of claim 1 wherein the passive movement is pressure applied and/or pivoting and/or movement to a support.

25. The method of claim 1 wherein one part of the object is stabilized with respect to another part of the object.

26. The method of claim 1 wherein a support surface can be pivoted about a first horizontal axis and a second axis that is inclined in a horizontal plane relative to the a vertical plane.

27. The method of claim 1 wherein the means for acquisition of the image has a bore passage.

28. An imaging device comprising:
    means for continuous real-time acquisition of an image of an object;
    a device for supporting the object to be imaged, the supporting device comprising
        at least one first support surface for a body or at least one first body part;
        means for stabilizing the body or the at least one first body part;
        means for fixing the body or the at least one first body part with the at least one first support surface;
        means for pivoting and/or applying pressure and/or movement to the at least one first support surface about a first axis to apply a defined reproducible passive movement to the body or at least one second body part while or during continuous imaging of the object in real-time;
        means for pivoting and/or applying pressure and/or movement to the at least one first support surface about a second axis independent of the first axis to apply a defined reproducible passive movement to the body or at least one second body part while or during continuous imaging of the object in real-time;
        means for applying a defined reproducible pressure to the at least one first support surface to thereby apply pressure and/or pivoting and/or movement to the body or at least one second body part while or during continuously imaging of the object in real-time; and
        means for sensing a pivotal position and/or applied pressure and/or movement to the at least one first support surface;
    a unit for controlling the means for pivoting and/or applied pressure and/or movement, the unit being disposed exterior to the imaging device;
    means for connecting the control unit with the means for pivoting and/or applied pressure and/or movement; and
    the means for connecting comprising a plurality of connections, each connection having an electrical ground and shielding against magnetic flux to avoid interference with the imaging, the ground and the shielding being disposed between the unit and the means for acquisition of an image and exterior to the means for acquisition of an image.

29. The imaging device of claim 28 comprising:
    a unit for attaching the device to a platform for receiving the object to be imaged.

30. The imaging device of claim 28 wherein the shielding against magnetic flux is at least one ferrite core arranged on each means for connecting.

31. The imaging device of claim 28 wherein the means for connecting comprises an infrared remote control.

32. The imaging device of claim 28 comprising a non-pivoting support surface for at least one third body part.

33. The imaging device of claim 28 wherein the supporting device is made from materials that reduce or avoid interferences or artifacts in the imaging.

34. The imaging device of claim 33 wherein the material is non-ferromagnetic.

35. The imaging device of claim 34 wherein the material is a plastic transparent to radiation.

36. The imaging device of claim 28 wherein the means for sensing comprises at least one optical encoder.

37. The imaging device of claim 28 wherein the object is disposed in a passage subject to an influence selected from the group consisting of a magnetic field, nuclear and emitted radiation.

38. The imaging device of claim 28 wherein the image is acquired in a magnetic resonance modality.

39. The imaging device of claim 28 wherein the image is acquired in a computer tomography modality.

40. The imaging device of claim 28 wherein the image is acquired in an X-ray modality.

41. The imaging device of claim 28 wherein the image is acquired in an ultrasound modality.

42. The imaging device of claim 28 wherein the means for applying pressure and/or pivoting and/or movement is pneumatic or hydraulic.

43. The imaging device of claim 28 wherein the means for applying pressure and/or pivoting and/or movement is selected from the group consisting of continuous, constant, adjustable, step-by-step, variable and a combination thereof.

44. The imaging device of claim 28 wherein the means for applying pressure and/or pivoting and/or movement is a non-ferromagnetic drive motor.

45. The imaging device of claim 44 wherein the motor is a piezoelectric.

46. The device of claim 28 wherein the pivoting and/or the applied pressure and/or movement reproduces stress on the at least one second part of the object.

47. The device of claim 28 wherein the means for applying pressure and/or pivoting and/or movement is a non-ferromagnetic motor.

48. The device of claim 28 wherein the means for acquisition has a closed bore imaging passage.

49. The device of claim 28 wherein the pivoting and/or the applied pressure and/or movement reproduces stress on the body of the object or the at least one first body part.

50. The imaging device of claim 28 wherein the means for acquisition of the image has a bore passage.

51. A method for acquiring an image of an anatomical body having a joint or an anatomical body part having a joint comprising:
provided for the continuous real-time acquisition of the image of the body or the body part by magnetic resonance imaging;
providing a device for stabilizing one part of the body or the body part, the device formed of a material that avoids interferences or artifacts in the acquired image;
applying to a second part of the body or the body part while or during continuously acquiring an image a defined reproducible passive movement of an applied pressure and/or movement and/or pivoting by a non-ferromagnetic motor that is continuous or constant or adjustable or step-by-step or variable or a combination thereof;
providing a defined reproducible pivoting of the body or the body part by a non-ferromagnetic motor while or during continuously acquiring an image about first and second independent axes with respect to the body or the body part;
providing a unit for controlling the pivoting and passive movement;
disposing the unit exterior to the magnetic resonance acquisition;
providing between the unit and the magnetic resonance acquisition and exterior to the magnetic resonance acquisition a plurality of electrically grounded connections from the unit to the magnetic resonance acquisition;
providing between the unit and the magnetic resonance acquisition and exterior to the magnetic resonance acquisition a plurality of connections, each connection having at least one ferrite core arranged on the connection for shielding against magnetic flux; and
acquiring the image of the physiological movement of the body or body part continuously in real-time while or during the pivoting and/or movement and/or applying pressure to the second body part.

52. The method of claim 51 wherein the pivoting and/or the applied pressure and/or movement reproduces stress on the second part of body.

53. The method of claim 51 wherein the magnetic resonance acquisition has a closed bore imaging passage.

54. The method of claim 51 wherein the pivoting and/or the applied pressure and/or movement reproduces stress on the body or the body part of the object.

55. The method of claim 51 wherein the motor is piezoelectric.

56. The method of claim 51 wherein the acquisition of the image has a bore passage.

57. An imaging device comprising:
means for continuous real-time magnetic resonance image acquisition of an anatomical body or anatomical body part;
a device for supporting the body or body part to be imaged, the supporting device formed of a material that avoids interferences or artifacts in the acquired image; comprising:
a support surface for the body or body part;
means for stabilizing one part of the body or body part;
means for fixing the body or body part with the support surface;
a non-ferromagnetic motor for pivoting the support surface about a first axis to apply a defined reproducible passive movement to another part of the body or body part while or during the continuous imaging of the body in real-time;
a non-ferromagnetic motor for pivoting the support surface about a second axis independent of the first axis to apply a defined reproducible passive movement to the another part of the body or body part while or during the continuous imaging of the body or body part in real-time;
a non-ferromagnetic drive for applying a defined reproducible pressure and/or pivoting and/or movement to the support surface to thereby apply pressure and/or pivoting and/or movement to the another part of the body or body part while or during the continuous imaging of the body or body part in real-time; and
means for sensing a pivotal position and/or applied pressure and/or movement and/or pivoting to the support surface;
a unit for controlling the motor for pivoting and the means for applying pressure and/or movement and/or pivoting, the unit being disposed exterior to the means for magnetic resonance image acquisition;
a plurality of connectors for connecting the control unit with the motor for pivoting and the means for applying pressure and/or movement and/or pivoting; and
each connector having an electrical ground and a ferrite core shielding against magnetic flux to avoid interference with the means for magnetic resonance imaging acquisition, the ground and the shielding being disposed between the unit and the means
for magnetic resonance image acquisition and exterior to the means for magnetic resonance image acquisition.

58. The device of claim 57 wherein the pivoting and/or the applied pressure and/or movement reproduces stress on the another part of the body.

59. The device of claim 57 wherein the means for acquisition has a closed bore imaging passage.

60. The device of claim 57 wherein the pivoting and/or the applied pressure and/or movement reproduces stress on the body or the body part of the object.

61. The device of claim 57 wherein the motor is piezoelectric.

62. The imaging device of claim 57 wherein the means for acquisition of the image has a bore passage.

63. The imaging device of claim 57 wherein the passive movement and/or the pressure and/or pivoting is continuous or constant or adjustable or step-by-step or variable or a combination thereof.

64. An imaging device comprising:
means for continuous real-time acquisition of an image of an object;
a support for the object or at least one body part of the object to be imaged;
a non-ferromagnetic drive for pivoting and/or applying pressure and/or movement about a first and a second independent axis to apply a defined reproducible passive movement to the object or the at least one body part or the support while or during continuous imaging of the object in real-time;
a unit for controlling the drive for pivoting and/or applied pressure and/or movement; and
means for connecting the control unit with the drive for pivoting and/or applied pressure and/or movement.

65. The imaging device of claim 64 wherein the unit is disposed exterior to the imaging device.

66. The imaging device of claim 64 wherein the means for connecting comprising at least a connection that is disposed between the unit and the means for acquisition of the image and exterior to the means for acquisition of an image.

67. The imaging device of claim 66 wherein the means for connecting comprises an electrical ground and/or shielding against magnetic flux to avoid interference with the imaging, the ground and/or the shielding being disposed between the unit and the means for acquisition of an image and exterior to the means for acquisition of an image.

68. The imaging device of claim 67 wherein the shielding against magnetic flux is at least one ferrite core arranged on the means for connecting.

69. The imaging device of claim 64 wherein the support is made from materials that reduce or avoid interferences or artifacts in the imaging.

70. The imaging device of claim 69 wherein the material is non-ferromagnetic.

71. The imaging device of claim 64 wherein the device comprises means for sensing the pivoting and/or applied pressure and/or movement or the support.

72. The imaging device of claim 69 wherein the material is a plastic transparent to radiation.

73. The imaging device of claim 64 wherein the object or the at least one body part of the object is disposed in a passage subject to an influence selected from the group consisting of a magnetic field, nuclear and emitted radiation.

74. The imaging device of claim 64 wherein the image is acquired in a magnetic resonance modality.

75. The imaging device of claim 64 wherein the image is acquired in a computer tomography modality.

76. The imaging device of claim 64 wherein the image is acquired in an ultrasound modality.

77. The imaging device of claim 64 wherein the drive for applying pressure and/or pivoting and/or movement is selected from the group consisting of continuous, constant, adjustable, or step-by-step, variable and a combination thereof.

78. The imaging device of claim 64 wherein the drive is a piezoelectric.

79. The imaging device of claim 64 wherein the means for acquisition has a closed bore imaging passage.

80. The device of claim 64 wherein the support or the pivoting and/or the applied pressure an/or movement reproduces stress on the body of the object or the at least one body part.

81. The device of claim 64 wherein the first and second axes being at an incline with respect to each other.

82. The device of claim 64 wherein the drive for applying pressure and/or pivoting and/or movement imitates a physiological movement of the object or the at least one body part of the object.

83. The device of claim 64 wherein the object or the at least one body part of the object has a joint.

84. The device of claim 64 wherein the object or the at least one body part of the object is anatomical.

85. The device of claim 64 wherein the object or the at least one body part of the object is non-human.

86. The device of claim 64 wherein the drive for applying pressure and/or pivoting and or movement reproduces stress on the object or the at least one body part of the object.

87. The imaging device of claim 64 wherein the means for acquisition of the image has a bore passage.

88. A method for acquiring an image of an object or at least one body part of the object comprising:
providing means for continuous real-time acquisition of the image of the object or the at least one body part of the object;
providing a non-ferromagnetic support for the object or the at least one body part of the object;
providing a non-ferromagnetic drive for pivoting and/or applying pressure and/or movement about a first and a second independent axis to apply a defined reproducible passive movement to the support or the object or the at least one body part of the object while or during continuous imaging of the support or the object or the at least one body part of the object in real-time; and
acquiring the image continuously in real-time during imaging while or during applying the defined reproducible passive movement of pivoting and/or applying pressure and/or movement to the support or the object or the at least one body part of the object.

89. The method of claim 88 wherein the support is made from materials that reduce or avoid interferences or artifacts in the imaging.

90. The method of claim 89 wherein the material is a plastic transparent to radiation.

91. The method of claim 88 wherein the device comprises means for sensing the pivoting and/or applied pressure and/or movement or the support.

92. The method of claim 88 wherein the object is disposed in a passage subject to an influence selected from the group consisting of a magnetic field, nuclear and emitted radiation.

93. The method of claim 88 wherein the image is acquired in a magnetic resonance modality.

94. The method of claim 88 wherein the image is acquired in a computer tomography modality.

95. The method of claim 88 wherein the image is acquired in an ultrasound modality.

96. The method of claim 88 wherein the drive for applying pressure and/or pivoting and/or movement is selected from the group consisting of continuous, constant, adjustable, step-by-step, variable and a combination thereof.

97. The method of claim 88 wherein the drive is a piezoelectric.

98. The method of claim 88 wherein the means for acquisition has a closed bore imaging passage.

99. The method of claim 88 wherein the support or the pivoting and/or the applied pressure and/or movement reproduces stress on the body of the object or the at least one body part.

100. The method of claim 88 wherein the first and second axes being at an incline with respect to each other.

101. The method of claim 88 wherein the drive for applying pressure and/or pivoting and/or movement imitates a physiological movement of the object or the at least one body part of the object.

102. The method of claim 88 wherein the object or the at least one body part of the object has a joint.

103. The method of claim 88 wherein the object or the at least one body part of the object is anatomical.

104. The method of claim 88 wherein the object or the at least one body part of the object is non-human.

105. The method of claim 88 wherein the drive for applying pressure and/or pivoting and/or movement reproduces stress on the object or the at least one body part of the object.

106. The method of claim 88 wherein the means for acquisition of the image has a bore passage.

* * * * *